US012193794B2

(12) United States Patent
Li et al.

(10) Patent No.: US 12,193,794 B2
(45) Date of Patent: Jan. 14, 2025

(54) HEART PHYSIOLOGICAL PARAMETER MEASUREMENT SYSTEM AND TERMINAL, AND COMPUTER STORAGE MEDIUM

(71) Applicant: SHENZHEN DARMA TECHNOLOGY CO., LTD., Shenzhen (CN)

(72) Inventors: Yeping Li, Shenzhen (CN); Fei Ye, Shenzhen (CN); Shaochun Zhuang, Shenzhen (CN)

(73) Assignee: CARDIOSTORY INC., Lewes, DE (US)

( * ) Notice: Subject to any disclaimer, the term of this patent is extended or adjusted under 35 U.S.C. 154(b) by 843 days.

(21) Appl. No.: 17/274,785

(22) PCT Filed: Sep. 10, 2018

(86) PCT No.: PCT/CN2018/104869
§ 371 (c)(1),
(2) Date: Mar. 9, 2021

(87) PCT Pub. No.: WO2020/051741
PCT Pub. Date: Mar. 19, 2020

(65) Prior Publication Data
US 2022/0047171 A1 Feb. 17, 2022

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/1102* (2013.01); *A61B 5/1126* (2013.01);
(Continued)

(58) Field of Classification Search
None
See application file for complete search history.

(56) References Cited

U.S. PATENT DOCUMENTS

2015/0038856 A1    2/2015  Houlton et al.

FOREIGN PATENT DOCUMENTS

| CN | 101951831 A | 1/2011 |
| CN | 102458237 A | 5/2012 |

(Continued)

*Primary Examiner* — Benjamin S Melhus
(74) *Attorney, Agent, or Firm* — Cheng-Ju Chiang

(57) ABSTRACT

Provided are a heart physiological parameter measurement method, device and terminal, and a computer storage medium. The method comprises: respectively obtaining back vibration information and shoulder vibration information of an object to be measured in a supine state by means of one or more shoulder vibration sensitive sensors and back vibration sensitive sensors; respectively generating first hemodynamic related information and second hemodynamic related information on the basis of the back vibration information and the shoulder vibration information, the second hemodynamic related information comprising right shoulder second hemodynamic related information generated from right shoulder vibration information; determining a reference AVC time point of an AVC event on the basis of the first hemodynamic related information; and determining an AVC feature point of the AVC event on the basis of the reference AVC time point and the right shoulder second hemodynamic related information.

13 Claims, 5 Drawing Sheets

(51) Int. Cl.
    *A61B 5/11*          (2006.01)
    *A61B 5/318*       (2021.01)
    *A61B 5/02*         (2006.01)

(52) U.S. Cl.
    CPC ............ *A61B 5/318* (2021.01); *A61B 5/6892* (2013.01); *A61B 5/743* (2013.01); *A61B 5/02028* (2013.01); *A61B 2560/0223* (2013.01)

(56) References Cited

FOREIGN PATENT DOCUMENTS

| | | |
|---|---|---|
| CN | 108056769 A | 5/2018 |
| CN | 108057176 A | 5/2018 |

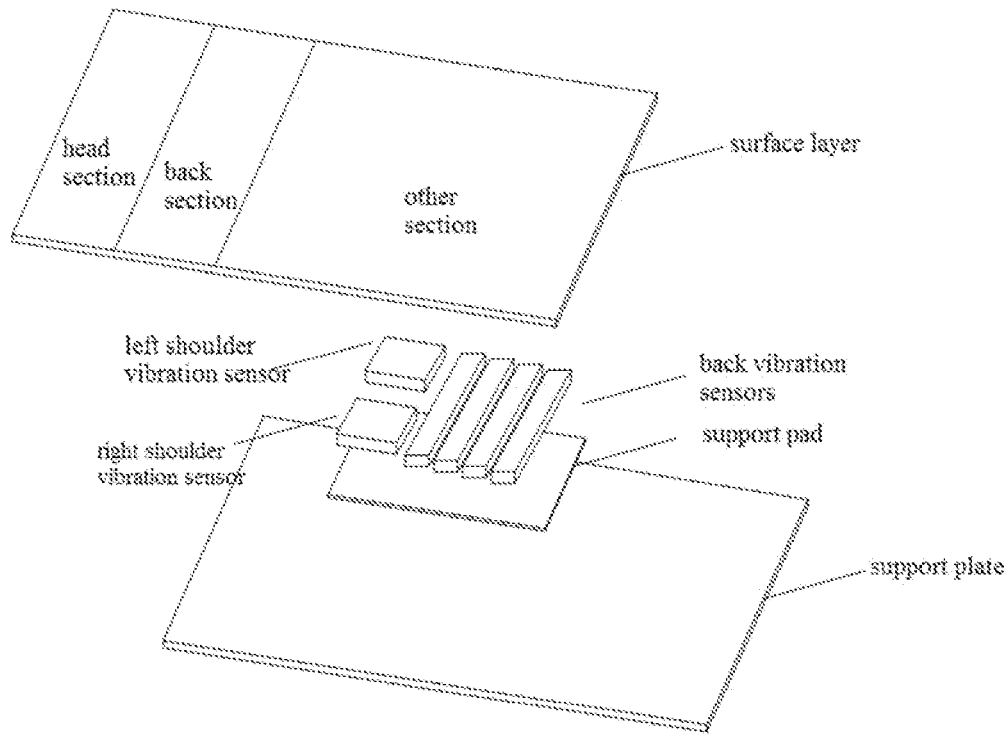

FIG. 3

| | |
|---|---|
| RESPECTIVELY OBTAIN BACK VIBRATION INFORMATION AND SHOULDER VIBRATION INFORMATION OF AN OBJECT TO BE MEASURED IN A SUPINE STATE BY MEANS OF ONE OR MORE SHOULDER VIBRATION SENSITIVE SENSORS AND BACK VIBRATION SENSITIVE SENSORS | 101 |
| RESPECTIVELY GENERATE FIRST HEMODYNAMIC RELATED INFORMATION AND SECOND HEMODYNAMIC RELATED INFORMATION ON THE BASIS OF THE BACK VIBRATION INFORMATION AND THE SHOULDER VIBRATION INFORMATION | 102 |
| DETERMINE A REFERENCE AVC TIME POINT OF THE AVC EVENT ON THE BASIS OF THE FIRST HEMODYNAMIC RELATED INFORMATION | 103 |
| DETERMINE AN AVC FEATURE POINT OF THE AVC EVENT ON THE BASIS OF THE REFERENCE AVC TIME POINT AND THE RIGHT SHOULDER SECOND HEMODYNAMIC RELATED INFORMATION | 104 |

FIG. 4

HEART PHYSIOLOGICAL PARAMETER MEASUREMENT SYSTEM AND TERMINAL, AND COMPUTER STORAGE MEDIUM

CROSS REFERENCE TO RELATED APPLICATIONS

The present application is a 35 U.S.C. § 371 National Phase conversion of International (PCT) Patent Application No. PCT/CN2018/104869, filed on Sep. 10, 2018, the disclosure of which is incorporated by reference herein. The PCT International Patent Application was filed and published in Chinese.

FIELD OF THE INVENTION

The present invention relates to the field of cardiac physiological parameter measurement, and particularly relates to a heart physiological parameter measurement method, a device, a terminal and a computer storage medium.

BACKGROUND OF THE INVENTION

Commonly used methods of cardiac function detection to obtain parameters are generally divided into two ways: methods on the basis of traumatic detection and methods on the basis of non-invasive detection.

Where the methods on the basis of traumatic detection to obtain parameters include: cardiac catheterization, such as coronary angiography to obtain cardiac physiological parameters; these methods on the basis of traumatic detection to obtain parameters likely cause harm to the tested subject, and cannot repeat the detection multiple times. Methods on the basis of non-invasive detection include methods of generating ECG/PCG, etc. These detection methods need to attach a sensor at a designated position on the human skin, and a long-term use will cause a certain psychological burden on the tested subject.

In summary, the methods of obtaining cardiac function parameters through traumatic detection or non-invasive detection will cause physical or psychological impacts on the test subject, and are therefore not suitable for long-term testing.

SUMMARY OF THE INVENTION

Accordingly, the present invention provides a cardiac physiological parameter measurement method, a device, a terminal and a computer storage medium. By means of the test subject lying on an information acquisition device, it provides a parameter measurement method that is almost insensitive to the user, which will not cause trauma to the test subject, nor will it cause physical or psychological impact, which is conducive to long-term monitoring.

The present invention proposes the following specific embodiments:

A cardiac physiological parameter measurement method provided in accordance with the embodiments of the present invention, is applied to an information acquisition device provided with one or more vibration sensors, and comprises steps of:

respectively acquiring back vibration information and shoulder vibration information of a subject to be measured in a supine state by means of one or more shoulder vibration sensors and back vibration sensors; wherein, the back vibration sensors are configured to be placed under the back of the subject to be measured; the shoulder vibration sensors are configured to be placed under the shoulder of the subject to be measured; the shoulder vibration information comprises the right shoulder vibration information;

respectively generating first hemodynamic related information and second hemodynamic related information on the basis of the back vibration information and the shoulder vibration information, the second hemodynamic related information comprising right shoulder second hemodynamic related information generated from the right shoulder vibration information;

determining a reference AVC time point of an AVC event on the basis of the first hemodynamic related information, and determining an AVC feature point of the AVC event on the basis of the reference AVC time point and the right shoulder second hemodynamic related information.

In a specific embodiment, the vibration sensor is selected from one or more of: an acceleration sensor, a speed sensor, a displacement sensor, a pressure sensor, a strain sensor, a stress sensor, or sensors that convert physical quantities equivalently on the basis of acceleration, speed, pressure, or displacement.

In a specific embodiment, the strain sensor is a fiber-optic sensor.

In a specific embodiment, the shoulder vibration sensors include a left shoulder vibration sensor and a right shoulder vibration sensor;

the left shoulder vibration sensor is configured to be placed under the left shoulder blade of the subject to be measured;

the right shoulder vibration sensor is configured to be placed under the right shoulder blade of the subject to be measured.

In a specific embodiment, the sensing area of the left shoulder vibration sensor covers the shoulder section corresponding to the left shoulder blade of the subject to be measured;

the sensing area of the right shoulder vibration sensor covers the shoulder section corresponding to the right shoulder blade of the subject to be measured.

In a specific embodiment, the step of "respectively generating first hemodynamic related information and second hemodynamic related information on the basis of the back vibration information and the shoulder vibration information", comprises:

generating the first hemodynamic related information and the second hemodynamic related information by separately preprocessing the back vibration information and the shoulder vibration information, wherein the preprocessing comprises at least one of: filtering, denoising, and signal scaling.

In a specific embodiment, the step of "determining a reference AVC time point of an AVC event on the basis of the first hemodynamic related information", comprises:

extracting high-frequency component from the first hemodynamic related information to obtain a first high-frequency component signal waveform graph corresponding to the first hemodynamic related information; and performing a feature search on the first high-frequency component signal waveform graph by a feature search method to determine the reference AVC time point of the AVC event from the first high-frequency component signal waveform graph.

In a specific embodiment, when the vibration sensor is a fiber-optic sensor, the first high-frequency component signal waveform graph comprises: a second-order differential waveform graph or a fourth-order differential waveform graph;

in a specific embodiment, the step "performing a feature search on the first high-frequency component signal waveform graph by a feature search method to determine the reference AVC time point of the AVC event", comprises steps of:

determining a "M"-shaped feature peak group in the first high-frequency component signal waveform graph by a feature search method; and determining the reference AVC time point of the AVC event on the basis of the "M"-shaped feature peak group.

In a specific embodiment, when the first high-frequency component signal waveform graph is a second-order differential waveform graph, the step of "determining the reference AVC time point of the AVC event on the basis of the "M"-shaped feature peak group" comprises:

selecting the time point of the first wave peak in the "M"-shaped feature peak group as the reference AVC time point of the AVC event;

when the first high-frequency component signal waveform graph is a fourth-order differential waveform graph, the step of "determining the reference AVC time point of the AVC event on the basis of the "M"-shaped feature peak group" comprises:

selecting the time point of the first wave valley in the "M"-shaped feature peak group as the reference AVC time point of the AVC event.

In a specific embodiment, there are multiple first hemodynamic related information;

the step of "determining a reference AVC time point of an AVC event on the basis of the first hemodynamic related information" comprises:

for each of the first hemodynamic related information, respectively determining the first AVC feature point of the AVC event on the high-frequency component signal waveform graph corresponding to each of the first hemodynamic related information; and synchronizing the high-frequency component signal waveform graphs on the same time axis, and determining a reference AVC time point on the basis of each of the first AVC feature points.

In a specific embodiment, the step of "determining an AVC feature point of the AVC event on the basis of the reference AVC time point and the right shoulder second hemodynamic related information", comprises steps of:

synchronizing the high-frequency component signal waveform graphs corresponding to the first hemodynamic related information and the right shoulder second hemodynamic related information respectively on the same time axis;

determining a reference point at the same time as the reference AVC time point in the high-frequency component signal waveform graph corresponding to the right shoulder second hemodynamic related information; and selecting the first wave valley or the first wave peak on a left side of the reference point from the high-frequency component signal waveform graph corresponding to the right shoulder second hemodynamic related information as the AVC feature point of the AVC event.

In a specific embodiment, when the first wave valley or the first wave peak on a left side of the reference point cannot be determined from the high-frequency component signal waveform graph corresponding to the right shoulder second hemodynamic related information, use the reference AVC time point as the AVC time point of the AVC event.

In a specific embodiment, the step of "determining a reference AVC time point of an AVC event on the basis of the first hemodynamic related information" comprises:

graphically displaying the first hemodynamic related information; and displaying prompt information on a graphical display interface; wherein the prompt information is used to prompt calibration of the reference AVC time point of the AVC event;

determining a point of manual calibration on the graphical display interface; and setting the point as the reference AVC feature point of the AVC event.

In a specific embodiment, the shoulder vibration sensors comprise: a left shoulder vibration sensor configured to be placed under the left shoulder of the subject to be measured and a right shoulder vibration sensor configured to be placed under the right shoulder of the subject to be measured;

the second hemodynamic related information comprises left shoulder second hemodynamic related information generated from left shoulder vibration information.

The method further comprises:

performing second-order differential processing on the basis of the left shoulder second hemodynamic information to generate a second-order differential graph; and setting the highest peak in one cardiac cycle of the second-order differential graph as the AVO feature point of the AVO event.

In a specific embodiment, the method further comprises:

synchronizing the left shoulder second hemodynamic related information and the right shoulder second hemodynamic related information on the same time axis; and determining LVET on the basis of the corresponding time points of AVO feature point and AVC feature point in the same cardiac cycle.

In a specific embodiment, the method further comprises:

outputting the determined LVET and/or the information of the AVC feature point and/or the information of the AVO feature point.

In a specific embodiment, the method further comprises:

respectively performing a peak search on the signal waveform graph corresponding to the second hemodynamic related information; and setting the time interval corresponding to the waveform between the two adjacent highest peaks as one cardiac cycle.

In a specific embodiment, the method further comprises:

respectively acquiring the back vibration information and shoulder vibration information of the subject to be measured in the supine state by means of the back vibration sensor and the shoulder vibration sensor, and simultaneously acquiring the synchronous detection electrocardiogram of the subject to be measured; and determining the cardiac cycle on the basis of the synchronized detection electrocardiogram.

In a specific embodiment, there are one or more back vibration sensors arranged; and the back vibration sensors are configured to be placed under the back of the subject to be measured.

In a specific embodiment, the back vibration sensors are configured to be placed under the corresponding part of the vertebrae and/or ribs of the subject to be measured.

In a specific embodiment, the back vibration sensors are distributed in a strip shape along the height direction of the human body of the subject to be measured.

The embodiment of the present invention also provides a cardiac physiological parameter measurement device, which is applied to an information acquisition device provided with one or more vibration sensors, and comprises:

an acquisition unit, for respectively acquiring back vibration information and shoulder vibration information of a subject to be measured in a supine state by means of one or more shoulder vibration sensors and back vibration sensors; wherein, the back vibration sensors are configured to be placed under the back of the subject to be measured; the shoulder vibration sensors are configured to be placed under the shoulder of the subject to be measured; the shoulder vibration information comprises the right shoulder vibration information;

a generating unit, for respectively generating first hemodynamic related information and second hemodynamic related information on the basis of the back vibration information and the shoulder vibration information, the second hemodynamic related information comprising right shoulder second hemodynamic related information generated from the right shoulder vibration information;

a first determining unit, for determining a reference AVC time point of an AVC event on the basis of the first hemodynamic related information; and a second determining unit, for determining an AVC feature point of the AVC event on the basis of the reference AVC time point and the right shoulder second hemodynamic related information.

The embodiment of the present invention also provides a terminal, which is applied to an information acquisition device provided with one or more vibration sensors, and comprises:

a processor; and a memory storing instructions executable by the processor;

wherein the processor is used to perform:

respectively acquiring back vibration information and shoulder vibration information of a subject to be measured in a supine state by means of one or more shoulder vibration sensors and back vibration sensors; wherein, the back vibration sensors are configured to be placed under the back of the subject to be measured; the shoulder vibration sensors are configured to be placed under the shoulder of the subject to be measured; the shoulder vibration information comprises the right shoulder vibration information;

respectively generating first hemodynamic related information and second hemodynamic related information on the basis of the back vibration information and the shoulder vibration information, the second hemodynamic related information comprising right shoulder second hemodynamic related information generated from the right shoulder vibration information;

determining a reference AVC time point of an AVC event on the basis of the first hemodynamic related information, and determining an AVC feature point of the AVC event on the basis of the reference AVC time point and the right shoulder second hemodynamic related information.

The embodiment of the present invention also provides a computer storage medium, which is applied to an information acquisition device provided with one or more vibration sensors, and stores one or more computer programs thereon, and the one or more computer programs are executed to perform the following processes:

process A: respectively acquiring back vibration information and shoulder vibration information of a subject to be measured in a supine state by means of one or more shoulder vibration sensors and back vibration sensors; wherein, the back vibration sensors are configured to be placed under the back of the subject to be measured; the shoulder vibration sensors are configured to be placed under the shoulder of the subject to be measured; the shoulder vibration information comprises the right shoulder vibration information;

process B: respectively generating first hemodynamic related information and second hemodynamic related information on the basis of the back vibration information and the shoulder vibration information, the second hemodynamic related information comprising right shoulder second hemodynamic related information generated from the right shoulder vibration information;

process C: determining a reference AVC time point of an AVC event on the basis of the first hemodynamic related information, and process D: determining an AVC feature point of the AVC event on the basis of the reference AVC time point and the right shoulder second hemodynamic related information.

The embodiment of the present invention also provides a cardiac physiological parameter measurement system, comprising: an information acquisition device and an information processing device; and the information acquisition device comprises one or more vibration sensors.

The information acquisition device is used to respectively acquire back vibration information and shoulder vibration information of a subject to be measured in a supine state by means of one or more shoulder vibration sensors and back vibration sensors; wherein, the back vibration sensors are configured to be placed under the back of the subject to be measured; the shoulder vibration sensors are configured to be placed under the shoulder of the subject to be measured; the shoulder vibration information comprises the right shoulder vibration information;

the information processing device is used to:

respectively generate first hemodynamic related information and second hemodynamic related information on the basis of the back vibration information and the shoulder vibration information, wherein, the second hemodynamic related information comprises right shoulder second hemodynamic related information generated from the right shoulder vibration information;

determine a reference AVC time point of an AVC event on the basis of the first hemodynamic related information; and determine an AVC feature point of the AVC event on the basis of the reference AVC time point and the right shoulder second hemodynamic related information.

Accordingly, the present invention provides a cardiac physiological parameter measurement method, a device, a terminal and a computer storage medium. The method is applied to an information acquisition device provided with one or more vibration sensors, and comprises steps of: respectively acquiring back vibration information and shoulder vibration information of a subject to be measured in a supine state by means of one or more shoulder vibration sensors and back vibration sensors; wherein, the back vibration sensors are configured to be placed under the back of the subject to be measured; the shoulder vibration sensors are configured to be placed under the shoulder of the subject to be measured; the shoulder vibration information comprises the right shoulder vibration information; respectively generating first hemodynamic related information and second hemodynamic related information on the basis of the back vibration information and the shoulder vibration information, wherein the second hemodynamic related information comprising right shoulder second hemodynamic related information generated from the right shoulder vibration information; determining a reference AVC time point of an AVC event on the basis of the first hemodynamic related information, and determining an AVC feature point of the AVC event on the basis of the reference AVC time point and the right shoulder second hemodynamic related information. In this invention, the test subject lies on an information acquisition device, it provides a parameter measurement method that is almost insensitive to the user, which will not cause trauma to the test subject, nor will it cause physical or psychological impact, which is conducive to long-term monitoring.

BRIEF DESCRIPTION OF THE DRAWINGS

In order to explain the technical solutions of the embodiments of the present invention more clearly, the following will briefly introduce the drawings needed in the embodiments. It should be understood that the following drawings only show certain embodiments of the present invention, and therefore should not be regarded as a limitation of the scope. For those of ordinary skill in the art, other related drawings can be obtained from these drawings without creative work.

FIG. 3 is a schematic structural diagram of the information acquisition device in accordance with the embodiment of the present invention;

FIG. 4 illustrates a flowchart of a cardiac physiological parameter measurement method in accordance with the embodiment of the present invention;

DETAILED DESCRIPTION OF THE INVENTION

Hereinafter, various embodiments of the present invention will be described more fully. The present invention may have various embodiments, and adjustments and changes may be made therein. However, it should be understood that there is no intention to limit the present invention to the specific embodiments disclosed herein, but the present invention should be understood to cover all adjustments, equivalents and/or alternatives within the spirit and scope of various embodiments of the present invention.

The terms used in various embodiments of the present invention are only used for the purpose of describing specific embodiments and are not intended to limit various embodiments of the present invention. As used herein, the singular form is intended to also include the plural form, unless the context clearly states. Unless otherwise defined, all terms (including technical and scientific terms) used herein have the common meanings as being understood by those of ordinary skill in the art which the embodiments of the present invention belong to. The terms (such as those defined in commonly used dictionaries) will be interpreted according to the contextual in the related technical field and will not be interpreted as idealized or overly formal meanings, unless clearly defined in the embodiments of the present invention.

Embodiment 1

Figure 1:
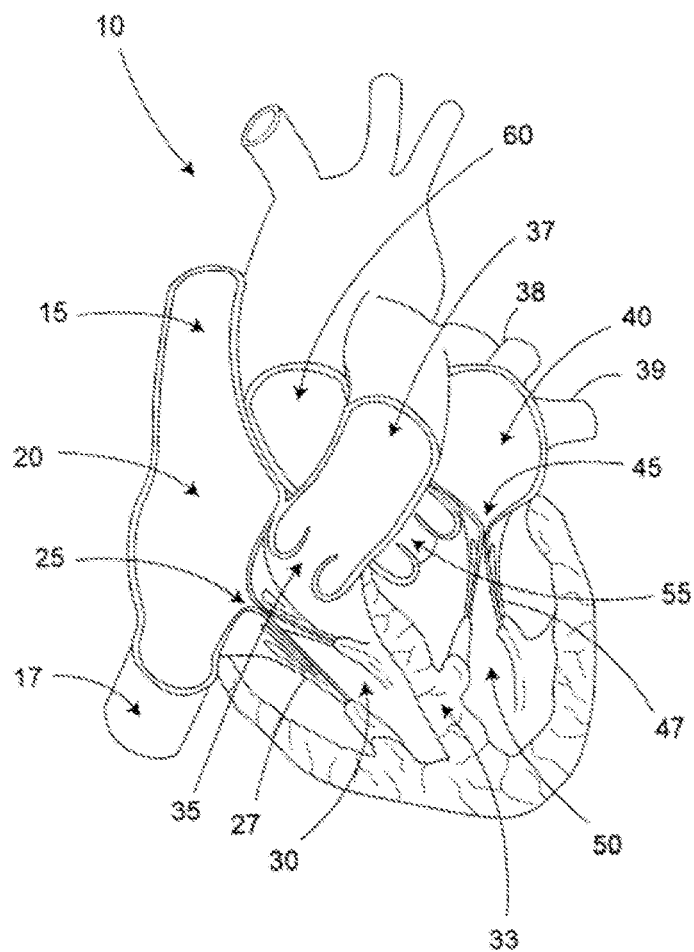
FIG. 1 is a schematic diagram illustrating the heart structure in accordance with an embodiment of the present invention.

The embodiment of the present invention provides a cardiac physiological parameter measurement method, for acquiring cardiac physiological parameters, as shown in FIG. 1, the heart structure and the mechanical process of heart beat are as follows: the heart 10 includes four chambers, the right atrium 20 and the right ventricle 30 that are connected to each other through the tricuspid valve 25, and the left atrium 40 and the left ventricle 50 that are connected to each other through the mitral valve 45. The blood flows back to the right atrium 20 via the superior vena cava 15 from the upper half of the body and via the inferior vena cava 17 from the lower half of the body. The myocardium of the right atrium 20 and the papillary muscle 27 of the right ventricle 30 simultaneously contract to open the tricuspid valve 25, so that blood can flow from the right atrium 20 into the right ventricle 30, and then the tricuspid valve 25 closes when the papillary muscle 27 relaxes. When the myocardium of the right ventricle 30 contracts, blood flows from the right ventricle 30 through the pulmonary valve 35 (labeled to both sides of the valve rather than the hole) into the pulmonary artery 37, which transports the blood to the lungs, where the blood is oxidized. The oxidized blood returns to the left atrium 40 through the pulmonary veins 38 and 39. The myocardium of the left atrium 40 and the papillary muscle 47 of the left ventricle 50 contract simultaneously, the mitral valve 45 opens so that oxidized blood flows from the left atrium 40 into the left ventricle 50, and then the papillary muscle 47 relaxes to allow the mitral valve 45 to close. Then, the left ventricle 50 compresses the oxidized blood to flow through the aortic valve 55 to enter the aorta 60, and the aorta 60 delivers the oxidized blood to the entire body via the peripheral vascular system.

The cyclical beating of the heart will cause various periodic changes, such as intracardiac pressure and cardiovascular pressure, the volume of the atria and ventricles, periodic changes in opening and closing of intracardiac valves (including mitral valve, tricuspid valve, aortic valve, pulmonary valve), and blood flow speed, etc. These changes drive blood to flow in a certain direction in the blood vessel. Hemodynamics studies dynamics of blood flow in the cardiovascular system, which aims to blood flow and blood vessel wall deformation. The "hemodynamic related information" described in this invention refers to any hemodynamic related information, which can include, but not limited to, one or more of: information related to blood flow generation (for example, heart's ejection caused by the contraction and relaxation of the heart), and blood flow-related information (such as cardiac output CO, left ventricular ejection impacting the aortic arch), blood pressure-related information (such as systolic arterial pressure, diastolic blood pressure, mean arterial pressure), or blood vessel-related information (for example, vascular elasticity). The cyclical beating of the heart can maintain blood circulation. Therefore, various parameters related to the beating of the heart, such as opening and closing of the intracardiac valve, changes in the volume of the atria and ventricles, etc., are all hemodynamic related information.

This invention discloses a method: measuring the vibration information of the human body; obtaining hemodynamic related information from the vibration information of the human body, and then obtaining the required vital sign information (for example, various parameters for the heartbeat) from the hemodynamic related information. Therefore, in accordance with this invention, acquire vibration information of the body using an information acquisition device first, and then extract hemodynamic related information from the vibration information (including cardiac vibration information and some information about blood flow).

And then, extract the AVC (Aortic Valve Closure) feature point and the AVO (Aortic Valve Opening) feature point from the hemodynamic related information.

Figure 2:
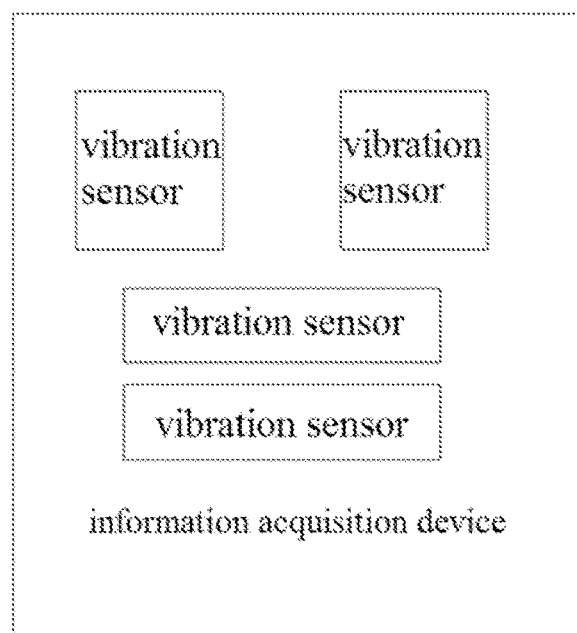
FIG. 2 is a schematic diagram of an information acquisition device in accordance with the embodiment of the present invention.

FIGS. 2-3 show a schematic diagram of an information acquisition device. The information acquisition device may include one or more vibration sensors, where each vibration sensor can be individually switched for data collection in a combination of multiple different vibration sensors; for example, only turning on the vibration sensor under the right shoulder of the subject to be measured and the vibration sensor under the back of the subject to be measured for data collection.

The location of each vibration sensor corresponds to different sections of the human body, and further, the vibration sensors may comprise any one or more combination selected from: an acceleration sensor, a speed sensor, a displacement sensor, a pressure sensor, a strain sensor, a stress sensor, or sensors (such as electrostatic sensors, inflatable micro-motion sensors, radar sensors, etc.) that convert physical quantities equivalently on the basis of acceleration, speed, displacement, or pressure. The strain sensor may be a fiber-optic strain sensor. The information acquisition device as shown in FIGS. 2-3 includes one or more vibration sensors. When the information acquisition device collects human body' vibration information, the subject to be measured needs to lie on its back on the information acquisition device; and the vibration sensor is configured to be disposed below the right shoulder of the subject to be measured, and can also be configured to be placed below the left shoulder and below the back of the subject to be measured. In some embodiments, the information acquisition device can also be implemented on a chair or other seating equipments. Specifically, the information acquisition device can be placed on a chair seat for the subject to sit on, or placed on the back of a chair for the subject to lean against.

Specifically, the vibration sensors may not directly contact the subject to be measured.

In some embodiments, the information acquisition device can be a cushion, the vibration sensor can be a fiber-optic sensor, and the subject to be measured needs to lie flat on it in a supine resting state, and the vibration sensor is used for vibration monitoring.

The principle of the fiber-optic sensor measuring body vibration is: when an external force is applied to the fiber-optic sensor, for example, when the human body lies flat on the cushion in a resting state, the human body's breathing and heartbeat will cause micro vibrations of the body. Micro vibration can make the bending of the optical fiber, which will change the parameters of light passing through the optical fiber, for example, changes in intensity of light. The changes in intensity of light after processing can be used to represent the body vibration.

As shown in FIG. 4, a cardiac physiological parameter measuring method 100 comprises the following steps:

step 101: respectively acquiring back vibration information and shoulder vibration information of a subject to be measured in a supine state by means of one or more shoulder vibration sensors and back vibration sensors; wherein, the back vibration sensors are configured to be placed under the back of the subject to be measured; the shoulder vibration sensors are configured to be placed under the shoulder of the subject to be measured; the shoulder vibration information comprises the right shoulder vibration information;

the shoulder vibration sensors include a left shoulder vibration sensor and a right shoulder vibration sensor;

the left shoulder vibration sensor is configured to be placed under the left shoulder blade of the subject to be measured;

the right shoulder vibration sensor is configured to be placed under the right shoulder blade of the subject to be measured.

Further, the sensing area of the left shoulder vibration sensor covers the shoulder section corresponding to the left shoulder blade of the subject to be measured; and the sensing area of the right shoulder vibration sensor covers the shoulder section corresponding to the right shoulder blade of the subject to be measured.

When the vibration sensor is disposed below the subject to be tested, the vibration information acquired by the vibration sensor may include: vibration information caused by breathing, body vibration information caused by contraction and relaxation of the heart, body vibration information caused by blood vessel wall deformation, and human body movement information (also known as body movement information). Body vibration information caused by contraction and relaxation of the heart can include body vibration information caused by the contraction and relaxation of the heart itself, as well as body vibration information caused by blood flow caused by contraction and relaxation of the heart, such as body vibration information caused by blood flowing in the aortic arch due to heart's ejection. Body vibration information caused by blood vessel wall deformation, can be caused by pulse wave propagating along blood vessels, where heart's ejection causes the aortic wall to expand to form a pulse wave. The body movement information can comprise leg bending, leg raising, turning over, shaking, etc. Specifically, breathing will cause the whole body, especially the body sections corresponding to the thorax and abdomen, to vibrate rhythmically. The contraction and relaxation of the heart will also cause the whole body, especially the body around the heart, to vibrate. The left ventricle pumps blood to the aorta, the blood will push against the aortic arch at the moment; and the heart itself and the connected large blood vessels as a whole will also undergo a series of movements. The farther the body part is from the heart, the weaker the vibration will be.

Step 102: respectively generating first hemodynamic related information and second hemodynamic related information on the basis of the back vibration information and the shoulder vibration information, the second hemodynamic related information comprising right shoulder second hemodynamic related information generated from the right shoulder vibration information;

the step of "respectively generating first hemodynamic related information and second hemodynamic related information on the basis of the back vibration information and the shoulder vibration information", comprises:

generating the first hemodynamic related information and the second hemodynamic related information by separately preprocessing the back vibration information and the shoulder vibration information, wherein the preprocessing comprises at least one of: filtering, denoising, and signal scaling.

For example, in one embodiment, filtering the vibration information (including the back vibration information and the shoulder vibration information) below 1 Hz, by means of but not limited to one or more of: low-pass filtering, band-pass filtering, IIR (Infinite Impulse Response) filtering, FIR (Finite Impulse Response) filtering, wavelet filtering, zero-phase bidirectional filtering, and polynomial fitting and smoothing filtering. The vibration information can be filtered at least once. If the vibration information carries power frequency interference, a power frequency filter can used to filter power frequency noise. Some high-frequency noise (for example, above 45 Hz) can also be filtered. The processed information can be scaled according to the situation to obtain hemodynamic related information.

Step 103: determining a reference AVC time point of an AVC event on the basis of the first hemodynamic related information.

Further, the step of "determining a reference AVC time point of an AVC event on the basis of the first hemodynamic related information", comprises:

extracting high-frequency component from the first hemodynamic related information to obtain a first high-frequency component signal waveform graph corresponding to the first hemodynamic related information; and performing a feature search on the first high-frequency component signal waveform graph by a feature search method to determine the reference AVC time point of the AVC event from the first high-frequency component signal waveform graph.

Specifically, when the vibration sensor is a fiber-optic sensor, the first high-frequency component signal waveform graph comprises: a second-order differential waveform graph or a fourth-order differential waveform graph;

in a specific embodiment, the step "performing a feature search on the first high-frequency component signal waveform graph by a feature search method to determine the reference AVC time point of the AVC event", comprises steps of:

determining a "M"-shaped feature peak group in the first high-frequency component signal waveform graph by a feature search method; and determining the reference AVC time point of the AVC event on the basis of the "M"-shaped feature peak group.

Figure 5:
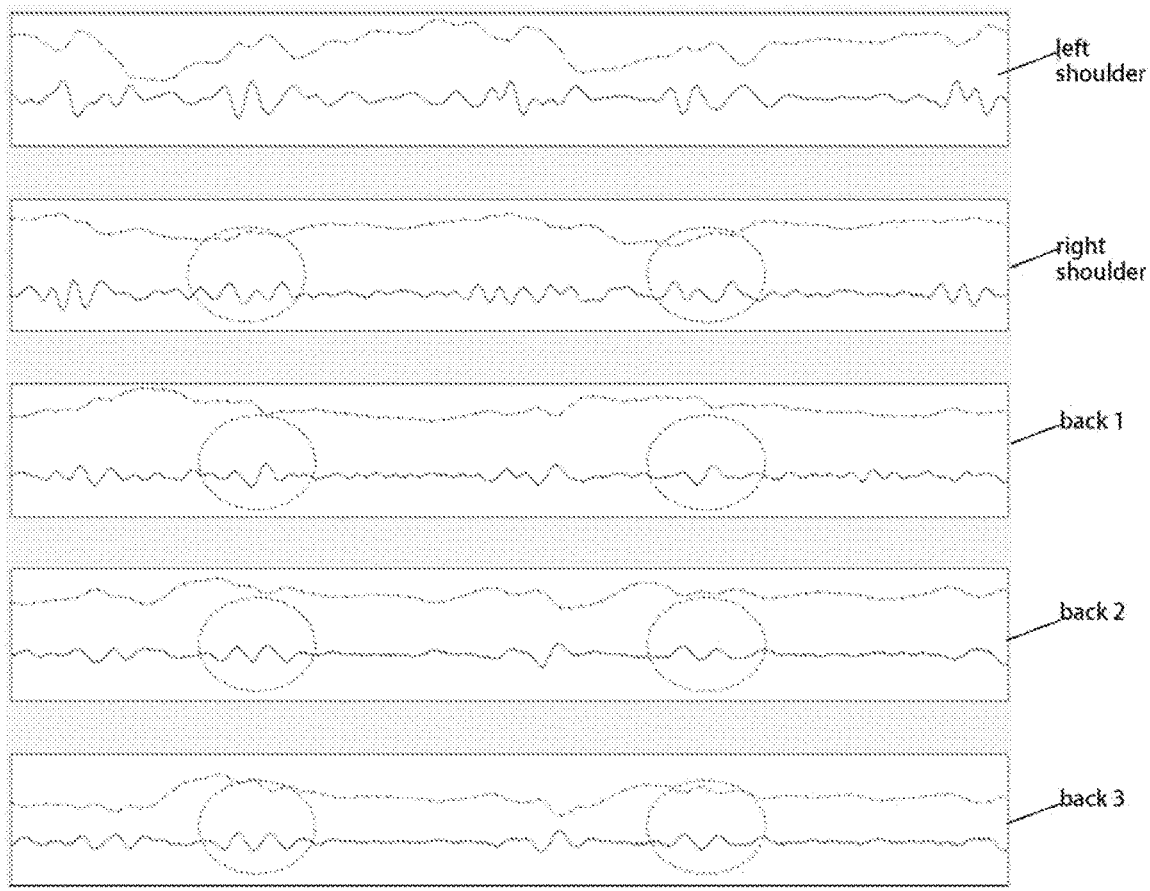
FIG. 5 illustrates waveform graphs of the hemodynamic related information and the corresponding high-frequency component signal waveform graphs in the cardiac physiological parameter measurement method in accordance with the embodiment of the present invention.
Figure 6:
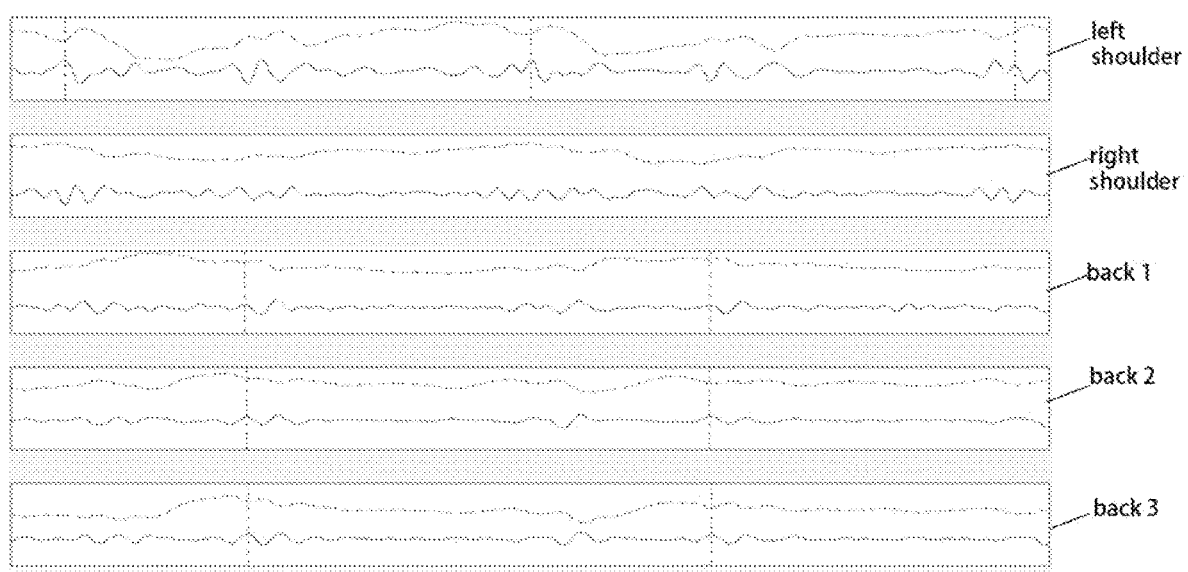
FIG. 6 illustrates waveform graphs of the hemodynamic related information and the corresponding high-frequency component signal waveform graphs in the cardiac physiological parameter measurement method in accordance with the embodiment of the present invention.

Specifically, as shown in FIGS. 5 and 6, from top to bottom, the signal graphs correspond to the left shoulder, the right shoulder, back 1, back 2, and back 3 (specifically, take the graphs correspond to the right shoulder as an example, one of which on the upper side is the graph corresponding to the right shoulder vibration information; the other on the lower side is the high-frequency component signal waveform graph corresponding to the hemodynamic related information, and the distribution in the other signal graphs is the same). In the FIGS., there are three signals on the back, but not limited to three, it can be one or multiple signals.

In some embodiments, the quality of the right shoulder vibration signal obtained by the right shoulder vibration sensor is not good, and there are many interference peaks in the high-frequency signal component waveform graph (for example, the second-order differential graph), as shown in the signal graph corresponding to the right shoulder in FIG. 5. It is difficult to identify accurate AVC feature peaks by processing the right shoulder vibration signal alone and easy to cause misidentification.

In this case, the signal corresponding to the right shoulder has no prominent regularity. Through experiments, it is found that when the AVC event is transmitted down the longitudinal direction of the human body (height direction), the difference is very small, so it can be on the basis of one or more signals corresponding to the back to strengthen or independently identify the AVC feature points of the signal graph corresponding to the right shoulder. The second-order differential waveform graph of the three vibration signals of back 1, back 2, and back 3, which are collected synchronously with the shoulder vibration signal, show obvious and consistent features, that is, obvious "M"-shaped feature peak groups (two consecutive peaks are connected to form an "M" shape; of course, it can also be regarded as a "W" shape. Since the waveform is continuous, the position of the peak and valley of the "M" shape is moved back by one state, that is, the "peak" is switched to the "valley", "valley" switches to "peak", correspondingly connect two continuous valleys into a "W" shape, which will not be repeated here), as indicated by the dashed circles in FIG. 5. Further, for identification of the feature points of the "M"-shaped feature peak group, for example, a peak in the M-shaped feature peak group is taken as the AVC feature point, as shown in FIG. 6, the AVC feature points of the second-order differential waveform graphs of the three signals corresponding to back 1, back 2, and back 3 are connected into a line, and it can be seen that the time can maintain a high degree of consistency.

Therefore, the reference AVC time point of the AVC event can be determined on the basis of the "M"-shaped feature peak group in the high-frequency component signal waveform graphs of one or more back vibration signals.

Specifically, the high-frequency component signal waveform graph can comprise a second-order differential waveform graph or a fourth-order differential waveform graph, therefore:

when the first high-frequency component signal waveform graph is a second-order differential waveform graph, the step of "determining the reference AVC time point of the AVC event on the basis of the "M"-shaped feature peak group" comprises:

selecting the time point of the first wave peak in the "M"-shaped feature peak group as the reference AVC time point of the AVC event;

when the first high-frequency component signal waveform graph is a fourth-order differential waveform graph, the step of "determining the reference AVC time point of the AVC event on the basis of the "M"-shaped feature peak group" comprises:

selecting the time point of the first wave valley in the "M"-shaped feature peak group as the reference AVC time point of the AVC event.

Specifically, for a better accuracy, there are multiple first hemodynamic related information;

In step 103, the step of "determining a reference AVC time point of an AVC event on the basis of the first hemodynamic related information" comprises:

for each of the first hemodynamic related information, respectively determining the first AVC feature point of the AVC event on the high-frequency component signal waveform graph corresponding to each of the first hemodynamic related information; and synchronizing the high-frequency component signal waveform graphs on the same time axis, and determining a reference AVC time point by integrating the time points on the basis of each of the first AVC feature points.

Specifically, for example, generating the first hemodynamic related information corresponding to the back 1, the back 2, and the back 3 respectively;

then, respectively determining the first AVC feature points of the AVC event on the high-frequency component signal waveform graphs corresponding to the three first hemodynamic related information.

determining the reference AVC time point for the three first AVC feature points by, for example, calculating the average over time.

Determining the reference AVC time point of the AVC event by manual calibration, specifically, the step of "determining a reference AVC time point of an AVC event on the basis of the first hemodynamic related information" comprises:

graphically displaying the first hemodynamic related information; and displaying prompt information on a graphical display interface; wherein the prompt information is used to prompt calibration of the reference AVC time point of the AVC event;

determining a point of manual calibration on the graphical display interface; and setting the point as the reference AVC time point of the AVC event.

Specifically, the graphical display interface may have a preset zoom display function, when manually calibrating points, the calibrating operator may zoom in the graphical display interface displaying the first hemodynamic related information to determine the reference AVC time point of the AVC event. The waveform graph corresponding to the first hemodynamic related information can also be set with different filter intervals, for example, any filter interval between 1-45 HZ can be set. The filter frequency interval can be different according to the actual situation, such as an interval of 1-20 HZ, an interval of 1-30 HZ, an interval of 1-35 HZ, an interval of 1-40 HZ, an interval of 2-20 HZ, an interval of 2-20 HZ, and an interval of any sub-range within 1-45 HZ, etc., for example, can also be an interval of 3-20 HZ, 3-21 HZ, 3-40 HZ, 3-25 HZ, 3-45 HZ, 5-20 HZ, 5-26 HZ, 5-40 HZ, or 5-45 HZ, and so on. The calibrating operator can independently select a filter interval according to the detail display of the waveform graph corresponding to the first hemodynamic related information, so as to obtain more detailed first hemodynamic related information by filtering to perform feature point calibration.

The manually calibrated point needs to be on the wave graph or the distance from the graph is less than a preset value, so as to avoid setting the point generated by false touch (such as the touch point caused by hand shaking) as the manually calibrated point. During the process, the operation of setting the current manually calibrated point as the reference AVC time point of the AVC event can be performed only when the calibrating operator further confirm.

Further, in order to prompt the calibrating operator to perform the calibration operation, prompt information may also be displayed on the graphic display interface; wherein the prompt information is used to prompt manually calibrating the reference AVC time point of the AVC event.

After determining the reference AVC time point, perform the following step 104.

Step 104: determining an AVC feature point of the AVC event on the basis of the reference AVC time point and the right shoulder second hemodynamic related information.

Specifically, in step 104 "determining an AVC feature point of the AVC event on the basis of the reference AVC time point and the right shoulder second hemodynamic related information", comprises steps of:

synchronizing the high-frequency component signal waveform graphs corresponding to the first hemodynamic related information and the right shoulder second hemodynamic related information respectively on the same time axis;

determining a reference point at the same time as the reference AVC time point in the high-frequency component signal waveform graph corresponding to the right shoulder second hemodynamic related information; and selecting the first wave valley or the first wave peak on a left side of the reference point from the high-frequency component signal waveform graph corresponding to the right shoulder second hemodynamic related information as the AVC feature point of the AVC event.

Figure 7:
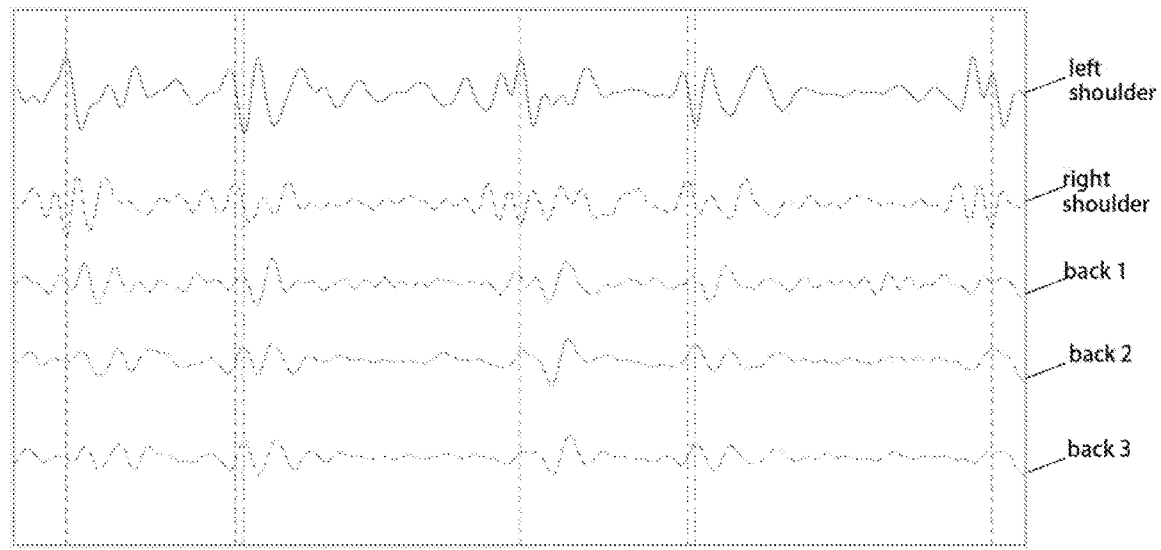
FIG. 7 illustrates waveform graphs of the hemodynamic related information and the corresponding high-frequency component signal waveform graphs in the cardiac physiological parameter measurement method in accordance with the embodiment of the present invention.

Specifically, as shown in FIG. 7, all the second-order differential waveforms graphs are drawn synchronously in the same chart 3 (the corresponding body parts from top to bottom are left shoulder, right shoulder, back 1, back 2, and back 3). It is easier to find that the time of the first peak of the "M"-shaped feature peak of each of the three second-order differential waveform graphs corresponding to back 1, back 2, and back 3 is almost the same. At this time, in the case that the signal characteristics corresponding to the right shoulder are not obvious, the multiple signals corresponding to the back are available to assist in the determination.

In one embodiment, the first peak on the left side of the reference point of the second-order differential waveform graph corresponding to the right shoulder is used as the AVC feature point. In FIGS. 5-7, according to second-order derivative graphs, the first wave peak of the second wave group is selected as the AVC feature point. In some cases, the first wave valley may be used as the AVC feature point.

In some embodiments, manual calibration can also be used to determine the AVC feature points:

specifically, synchronizing the high-frequency component signal waveform graphs corresponding to the first hemodynamic related information and the right shoulder second hemodynamic related information respectively on the same time axis, and displaying in a graphical interface;

determining a point of manual calibration on the graphical display interface; and if the point of manual calibration is on the high-frequency component signal waveform graph corresponding to the right shoulder second hemodynamic information, setting the point as the AVC feature point of the AVC event.

Specifically, on the graphical display interface, reference points can also be displayed graphically for reference during manual calibration.

In other embodiments, when the characteristics of the second-order derivative graph are not obvious, the fourth-order derivative graph can also be used. At the same time, the wave peak in the second-order derivative graph corresponds to the wave valley in the fourth-order derivative graph, and the wave valley in the second-order derivative graph corresponds to the wave peak in the fourth-order derivative graph. Therefore, if the fourth-order derivative graph is used for determination, the AVC feature point can be the first peak or valley of the fourth-order derivative graph corresponding to the right shoulder on the left side of the reference AVC time point.

Specifically, considering that the waveform in the high-frequency component signal waveform graph may not be significant, in this case, when the first wave valley or the first wave peak on the left side of the reference point cannot be determined in the high-frequency component signal waveform graph corresponding to the right shoulder second hemodynamic related information, the reference AVC time point is taken as the AVC time point of the AVC event.

Specifically, the shoulder vibration sensors comprise: a left shoulder vibration sensor configured to be placed under the left shoulder of the subject to be measured and a right shoulder vibration sensor configured to be placed under the right shoulder of the subject to be measured;

the second hemodynamic related information comprises left shoulder second hemodynamic related information generated from left shoulder vibration information;

therefore, in addition to determining the AVC feature points according to the right shoulder, the method can also comprise:

performing second-order differential processing on the basis of the left shoulder second hemodynamic information to generate a second-order differential graph; and setting the highest peak in one cardiac cycle of the second-order differential graph as the AVO feature point of the AVO event.

Figure 8:
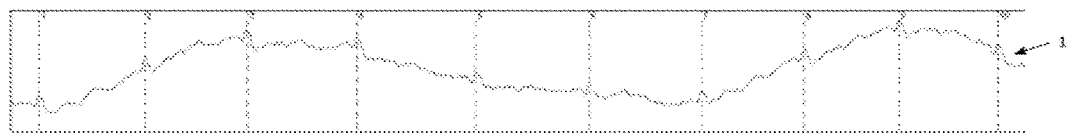
FIG. 8 illustrates a waveform graph of vibration information in the cardiac physiological parameter measurement method in accordance with the embodiment of the present invention.

FIG. 8 shows the waveform graph of the acquired vibration information according to the left shoulder of the subject to be measured. Graph 1 is the waveform diagram of the vibration information acquired by the vibration sensor under the left shoulder, where the horizontal axis represents time, and the vertical axis represents the normalized vibration information, which is dimensionless.

Figure 9:
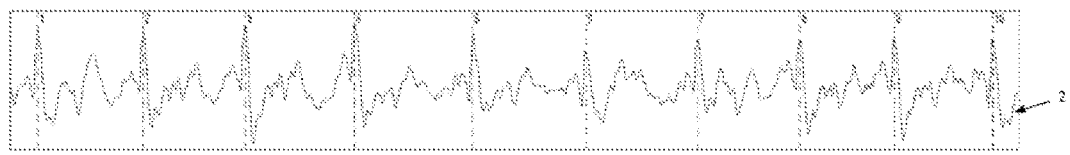
FIG. 9 illustrates waveform graphs of the hemodynamic related information in the cardiac physiological parameter measuring method in accordance with the embodiment of the present invention.

As shown in FIG. 9, graph 2 is a waveform diagram of the hemodynamic related information generated on the basis of left shoulder vibration information, in which the horizontal axis represents time. Specifically, graph 2 is the hemodynamic related information generated after filtering, denoising, and signal scaling on graph 1.

Figure 10:
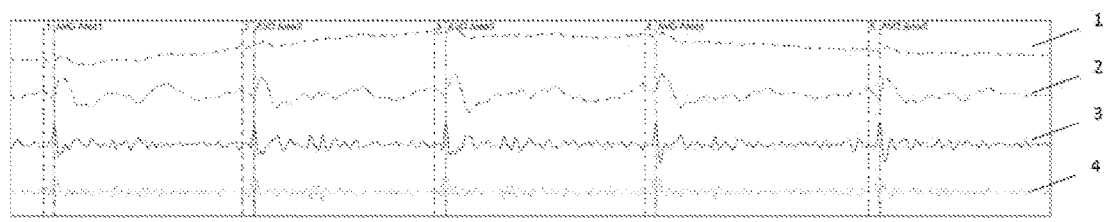
FIG. 10 illustrates multiple waveform graphs generated after processing the second hemodynamic related information in the cardiac physiological parameter measurement method in accordance with the embodiment of the present invention.

As shown in FIG. 10, graph 3 is a second-order differential waveform of the graph 2 after the second-order differential processing, and graph 4 is a fourth-order differential waveform of the graph 2 after the fourth-order differential processing. In a cardiac cycle, perform a peak search on graph 3, and the highest peak in a cardiac cycle is the AVO feature point.

After obtaining the AVO feature points, the method further comprises:

synchronizing the left shoulder second hemodynamic related information and the right shoulder second hemodynamic related information on the same time axis; and determining LVET on the basis of the corresponding time points of AVO feature point and AVC feature point in the same cardiac cycle.

Specifically, after determining the AVO feature points and AVC feature points, selecting the time points of AVO and AVC in a cardiac cycle, namely AVOT (Aortic Valve Opening Time) and AVCT (Aortic Valve Closure Time), and then determining LVET by the following formula:

$$LVET=AVCT-AVOT.$$

In a specific embodiment, the method further comprises: outputting, on a display, the determined LVET and/or the information of the AVC feature point and/or the information of the AVO feature point.

Specifically, when necessary, for example, when output instructions are received, the LVET and/or the information of the AVC feature point and/or the information of the AVO feature point may be output according to the output instructions.

Specifically, the vibration sensor obtains waveform in a continuous time, including data of several cardiac cycles, the total waveform in the graph need to be divided into cardiac cycles by means of the following method:

respectively performing a peak search on the signal waveform graph corresponding to the second hemodynamic related information; and setting the time interval corresponding to the waveform between the two adjacent highest peaks as one cardiac cycle.

Specifically, for example, a peak search can be performed on graph 2, and the waveform between the peak and the next peak is divided into a cardiac cycle, as shown in FIG. 9.

In addition, the determination of the cardiac cycle can also be done in the following ways:

respectively acquiring the back vibration information and shoulder vibration information of the subject to be measured in the supine state by means of the back vibration sensor and the shoulder vibration sensor, and simultaneously acquiring the synchronous detection electrocardiogram of the subject to be measured; and determining the cardiac cycle on the basis of the synchronized detection electrocardiogram. The specific synchronous detection electrocardiogram is ECG (Electrocardiograph).

Specifically, simultaneously acquiring the synchronous detection electrocardiogram of the subject to be measured. Since the electrocardiogram has electrodes connected, the waveforms thereof are stable and clear, which can be used as the division and calibration of the cardiac cycle to determine the cardiac cycle.

Further as shown in FIG. 3, there are one or more back vibration sensors arranged;

the back vibration sensors are configured to be placed under the back of the subject to be measured.

Multiple back vibration sensors can obtain more data to ensure higher accuracy.

In a specific embodiment, the back vibration sensors are distributed in a strip shape along the height direction of the human body of the subject to be measured.

Specifically, the back vibration sensors can theoretically be set to correspond to any position on the back, and are distributed in a long strip along the height of the human body. The width of the long strip can be changed; for example, can be 1 cm in width or 8 cm in width, etc. When the width of the strip is narrow, more rows of sensors can be arranged in an array, and obtain multiple rows of data and the accuracy will be higher; the width is wide, and vice versa. But there will be some waste if the width is narrow. The preferable width is 6-8 cm, and preferably three vibration sensors can be arranged, so that the data of each vibration sensor can be differentiated, and there will not be too many signals to increase the difficulty of data processing.

In a specific embodiment, the back vibration sensors are configured to be placed under the corresponding part of the vertebrae and/or ribs of the subject to be measured.

Specifically, considering the measurement of vibration, the quality of the vibration signal after being transmitted along the bones and muscles is better. Therefore, the preferable position of the back vibration sensor is set under the corresponding part of the vertebrae and/or ribs of the body.

Additionally, in the actual application, the following methods are also available to determine the AVC time point of an AVC event:

acquiring vibration information of the subject to be measured in a supine state by means of one or more vibration sensors; wherein the vibration sensors are configured to be placed under the right shoulder of the subject to be measured;

generating hemodynamic related information on the basis of the vibration information;

determining an AVC time point of the AVC event on the basis of the hemodynamic related information.

Specifically, processing the vibration information measured on the right shoulder to obtain hemodynamic related information, and then determining the AVC time point of the AVC event according to the hemodynamic related information.

In addition to determining the AVC time point of the AVC event directly on the basis of the vibration information measured on the right shoulder, the AVC time point of the AVC event can also be determined directly by using the vibration information obtained by the back vibration sensors.

Embodiment 2

Figure 11:
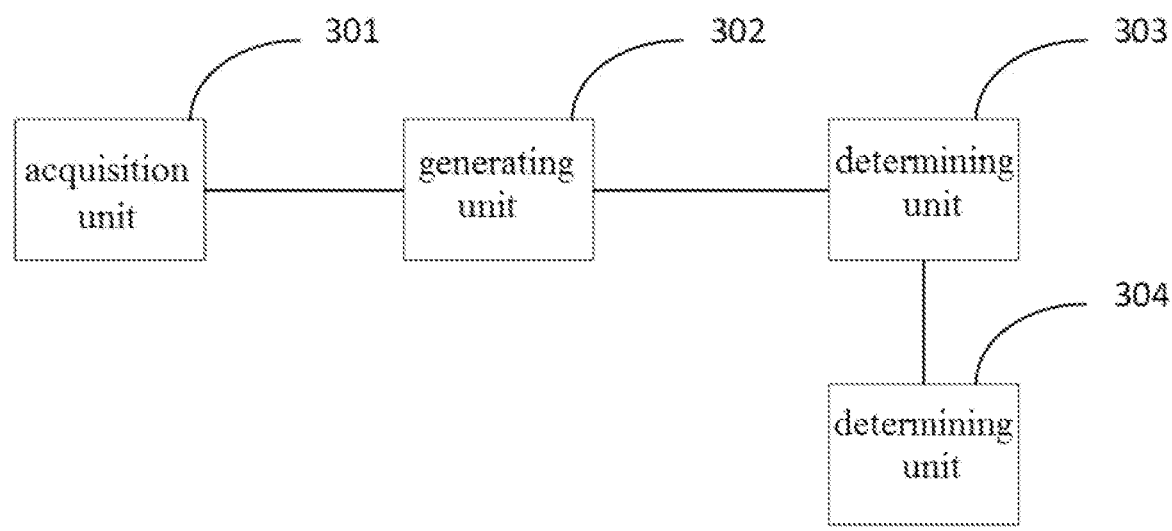
FIG. 11 is a structural block diagram of a cardiac physiological parameter measurement device in accordance with an embodiment of the present invention.

Embodiment 2 of the present invention provides a cardiac physiological parameter measurement device, which is applied to an information acquisition device provided with one or more vibration sensors, as shown in FIG. 11, and comprises:

an acquisition unit 301, for respectively acquiring back vibration information and shoulder vibration information of a subject to be measured in a supine state by means of one or more shoulder vibration sensors and back vibration sensors; wherein, the back vibration sensors are configured to be placed under the back of the subject to be measured; the shoulder vibration sensors are configured to be placed under the shoulder of the subject to be measured; the shoulder vibration information comprises the right shoulder vibration information;

a generating unit 302, for respectively generating first hemodynamic related information and second hemodynamic related information on the basis of the back vibration information and the shoulder vibration information, the second hemodynamic related information comprising right shoulder second hemodynamic related information generated from the right shoulder vibration information;

a first determining unit 303, for determining a reference AVC time point of an AVC event on the basis of the first hemodynamic related information; and a second determining unit 304, for determining an AVC feature point of the AVC event on the basis of the reference AVC time point and the right shoulder second hemodynamic related information.

Specifically, Embodiment 2 of the present invention also discloses other relevant technical features. For the specific relevant technical features, please refer to the description in Embodiment 1.

Embodiment 3

Figure 12:
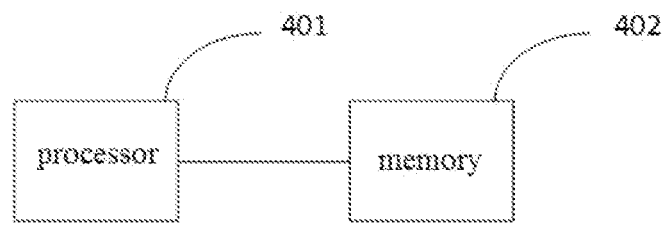
FIG. 12 is a structural block diagram of a terminal in accordance with an embodiment of the present invention.

Embodiment 3 of the present invention also provides a terminal, which is applied to an information acquisition device provided with one or more vibration sensors, as shown in FIG. 12, and comprises:

a processor 401; and a memory 402 storing instructions executable by the processor;

wherein the processor 401 are used to perform:

respectively acquiring back vibration information and shoulder vibration information of a subject to be measured in a supine state by means of one or more shoulder vibration sensors and back vibration sensors; wherein, the back vibration sensors are configured to be placed under the back of the subject to be measured; the shoulder vibration sensors are configured to be placed under the shoulder of the subject to be measured; the shoulder vibration information comprises the right shoulder vibration information; the one or more shoulder vibration sensors and back vibration sensors are connected with the processor;

respectively generating first hemodynamic related information and second hemodynamic related information on the basis of the back vibration information and the shoulder vibration information, the second hemodynamic related information comprising right shoulder second hemodynamic related information generated from the right shoulder vibration information;

determining a reference AVC time point of an AVC event on the basis of the first hemodynamic related information, and determining an AVC feature point of the AVC event on the basis of the reference AVC time point and the right shoulder second hemodynamic related information.

Specifically, Embodiment 3 of the present invention further discloses other relevant technical features. For the specific relevant technical features, please refer to the description in Embodiment 1.

Embodiment 4

Embodiment 4 of the present invention also provides a computer storage medium, which is applied to an information acquisition device provided with one or more vibration sensors, and stores one or more computer programs thereon, and the one or more computer programs are executed to perform the following processes:

process A: respectively acquiring back vibration information and shoulder vibration information of a subject to be measured in a supine state by means of one or more shoulder vibration sensors and back vibration sensors; wherein, the back vibration sensors are configured to be placed under the back of the subject to be measured; the shoulder vibration sensors are configured to be placed under the shoulder of the subject to be measured; the shoulder vibration information comprises the right shoulder vibration information;

process B: respectively generating first hemodynamic related information and second hemodynamic related information on the basis of the back vibration information and the shoulder vibration information, the second hemodynamic related information comprising right shoulder second hemodynamic related information generated from the right shoulder vibration information;

process C: determining a reference AVC time point of an AVC event on the basis of the first hemodynamic related information, and process D: determining an AVC feature point of the AVC event on the basis of the reference AVC time point and the right shoulder second hemodynamic related information.

Specifically, Embodiment 4 of the present invention further discloses other relevant technical features. For the specific relevant technical features, please refer to the description in Embodiment 1.

Embodiment 5

Embodiment 5 of the present invention also provides a cardiac physiological parameter measurement system, comprising: an information acquisition device and an information processing device; and the information acquisition device comprises one or more vibration sensors.

The information acquisition device is used to respectively acquire back vibration information and shoulder vibration information of a subject to be measured in a supine state by means of one or more shoulder vibration sensors and back vibration sensors; wherein, the back vibration sensors are configured to be placed under the back of the subject to be measured; the shoulder vibration sensors are configured to be placed under the shoulder of the subject to be measured; the shoulder vibration information comprises the right shoulder vibration information;

the information processing device is used to:

respectively generate first hemodynamic related information and second hemodynamic related information on the basis of the back vibration information and the shoulder vibration information, wherein, the second hemodynamic related information comprises right shoulder second hemodynamic related information generated from the right shoulder vibration information;

determine a reference AVC time point of an AVC event on the basis of the first hemodynamic related information; and determine an AVC feature point of the AVC event on the basis of the reference AVC time point and the right shoulder second hemodynamic related information.

Specifically, Embodiment 5 of the present invention further discloses other relevant technical features. For the specific relevant technical features, please refer to the description in Embodiment 1. In addition, the information acquisition device in Embodiment 5 of the present invention is the same as the information acquisition device in Embodiment 1, and the function of the information processing device corresponds to the method in Embodiment 1.

Embodiment 6

Embodiment 6 of the present invention provides a cardiac physiological parameter measurement method, is applied to an information acquisition device provided with one or more vibration sensors, and comprises steps of:

step 101: acquiring vibration information of the subject to be measured in a supine state by means of one or more vibration sensors; wherein the vibration sensors are configured to be placed under the right shoulder of the subject to be measured;

step 102: generating hemodynamic related information on the basis of the vibration information;

step 103: determining an AVC time point of the AVC event on the basis of the hemodynamic related information.

Specifically, Embodiment 6 of the present invention further discloses other relevant technical features. For the specific relevant technical features, please refer to the description in Embodiment 1. In addition, the information acquisition device in Embodiment 5 of the present invention is the same as the information acquisition device in Embodiment 1.

Those skilled in the art can understand that the accompanying drawings are only schematic diagrams of preferred implementation scenes, and the modules or processes in the accompanying drawings may not be necessarily for implementing the present invention.

Those skilled in the art can understand that the modules in the device in the implementation scene above can be distributed according to the description above, or can be changed to be located in one or more devices in different implementation scenes. The modules of the above implementation scene can be combined into one module or further divided into multiple sub-modules.

The labels of the present invention are only for description, and do not represent the pros and cons of implementation scenes.

What has been disclosed above are only a few specific implementation scenes of the present invention, but the present invention is not limited thereto, and any changes that can be thought of by those skilled in the art should fall into the protection scope of the present invention.

What is claimed is:

1. A cardiac physiological parameter measurement method which is performed by instructions executed by a processor of a terminal which comprises the processor and a memory storing the instructions executable by the processor, the method comprising steps of:

respectively acquiring back vibration information and shoulder vibration information of a subject to be measured in a supine state by means of one or more back vibration sensors and shoulder vibration sensors to generate waveforms of back vibration information and shoulder vibration information, and simultaneously acquiring a synchronous detection electrocardiogram of the subject to be measured; wherein, the back vibration sensors are configured to be placed under the back of the subject to be measured; the shoulder vibration sensors are configured to be placed under the shoulder of the subject to be measured; the shoulder vibration information comprises right shoulder vibration information; where the one or more back vibration sensors and shoulder vibration sensors are connected with the processor;

respectively generating first hemodynamic related information waveforms and second hemodynamic related information waveforms by preprocessing the back vibration information and the shoulder vibration information, wherein the preprocessing comprises at least one of: filtering, denoising, and signal scaling; the second hemodynamic related information waveforms comprise a right shoulder second hemodynamic related information waveform generated from the right shoulder vibration information;

determining cardiac cycles on the basis of the synchronized detection electrocardiogram;

extracting high-frequency component from the first hemodynamic related information waveform to obtain a first high-frequency component waveform;

performing a feature search on the first high-frequency component waveform to determine an M-shaped feature peak group in each cardiac cycle of the first high-frequency component waveform;

determining a reference Aortic Valve Closure Time (AVCT) of an Aortic Valve Closure (AVC) event on the basis of the M-shaped feature peak group;

determining an AVC feature point of the AVC event on the basis of the reference AVCT and the right shoulder second hemodynamic related information waveforms; and outputting the AVC feature point on a display connected with the processor.

2. The cardiac physiological parameter measurement method of claim 1, wherein said vibration sensor is selected from one or more of: an acceleration sensor, a speed sensor, a displacement sensor, a pressure sensor, a strain sensor, a stress sensor, or sensors that convert physical quantities equivalently on the basis of acceleration, speed, pressure, or displacement, the strain sensor is a fiber-optic sensor.

3. The cardiac physiological parameter measurement method of claim 1, wherein:
the shoulder vibration sensors include a left shoulder vibration sensor and a right shoulder vibration sensor;
the left shoulder vibration sensor is configured to be placed under the left shoulder blade of the subject to be measured;
the right shoulder vibration sensor is configured to be placed under the right shoulder blade of the subject to be measured;
a sensing area of the left shoulder vibration sensor covers the shoulder section corresponding to the left shoulder blade of the subject to be measured;
a sensing area of the right shoulder vibration sensor covers the shoulder section corresponding to the right shoulder blade of the subject to be measured.

4. The cardiac physiological parameter measurement method of claim 1, wherein when the vibration sensor is a fiber-optic sensor, the first high-frequency component waveform comprises: a second-order differential waveform or a fourth-order differential waveform.

5. The cardiac physiological parameter measurement method of claim 4, wherein when the first high-frequency component waveform is a second-order differential waveform, the step of determining the reference AVCT of the AVC event on the basis of the M-shaped feature peak group comprises:
selecting a time point of a first wave peak in the M-shaped feature peak group as the reference AVCT of the AVC event;
when the first high-frequency component waveform is a fourth-order differential waveform, the step of determining the reference AVCT of the AVC event on the basis of the M-shaped feature peak group comprises:
selecting a time point of a first wave valley in the M-shaped feature peak group as the reference AVCT of the AVC event.

6. The cardiac physiological parameter measurement method of claim 1, wherein there are multiple first hemodynamic related information waveforms;
the step of determining the reference AVCT of the AVC event comprises:
for each of the first hemodynamic related information waveforms, respectively determining the first AVC feature point of the AVC event on the high-frequency component waveform; and
synchronizing the high-frequency component waveforms on the same time axis, and determining the reference AVCT on the basis of each of the first AVC feature points.

7. The cardiac physiological parameter measurement method of claim 1, wherein the step of determining the AVC feature point of the AVC event, comprises:
synchronizing the first high-frequency component waveform and a second high-frequency component waveform of the right shoulder second hemodynamic related information waveform respectively on a same time axis;
determining, in the second high-frequency component waveform of the right shoulder second hemodynamic related information waveform, a reference point at the same time as the reference AVCT; and
selecting a first wave valley or a first wave peak on a left side of the reference point of the second high-frequency component waveform of the right shoulder second hemodynamic related information waveform as the AVC feature point of the AVC event.

8. The cardiac physiological parameter measurement method of claim 7, further comprising:
when the first wave valley or the first wave peak on a left side of the reference point cannot be determined from the second high-frequency component waveform of the right shoulder second hemodynamic related information waveform, using the reference AVCT as the AVCT of the AVC event.

9. The cardiac physiological parameter measurement method of claim 1, wherein there are one or more back vibration sensors arranged; and
the back vibration sensors are configured to be placed under the back of the subject to be measured.

10. The cardiac physiological parameter measurement method of claim 1, wherein the back vibration sensors are configured to be placed under the corresponding part of the vertebrae and/or ribs of the subject to be measured; and, the back vibration sensors are distributed along the body height direction of the subject to be measured.

11. A cardiac physiological parameter measurement method which is performed by instructions executed by a processor of a terminal which comprises the processor and a memory storing the instructions executable by the processor, comprising steps of:

respectively acquiring back vibration information and shoulder vibration information of a subject to be measured in a supine state by means of one or more back vibration sensors and shoulder vibration sensors to generate waveforms of back vibration information and shoulder vibration information, respectively, and simultaneously acquiring a synchronous detection electrocardiogram of the subject to be measured; wherein, the back vibration sensors are connected with the processor and configured to be placed under the back of the subject; the shoulder vibration sensors comprises a left shoulder vibration sensor connected with the processor and configured to be placed under the left shoulder of the subject and a right shoulder vibration sensor connected the processor and configured to be placed under the right shoulder of the subject; the shoulder vibration information comprises left and right shoulder vibration information;

respectively generating first hemodynamic related information waveforms and second hemodynamic related information waveforms by preprocessing the back vibration information and the shoulder vibration information, wherein the preprocessing comprises at least one of: filtering, denoising, and signal scaling; the second hemodynamic related information waveforms comprise a left shoulder second hemodynamic related information waveform and a right shoulder second hemodynamic related information waveform;

determining cardiac cycles on the basis of the synchronized detection electrocardiogram;

extracting high-frequency component from the first hemodynamic related information waveform to obtain a first high-frequency component waveform;

performing a feature search on the first high-frequency component waveform to determine an M-shaped feature peak group in each cardiac cycle of the first high-frequency component waveform;

determining a reference Aortic Valve Closure Time (AVCT) of an Aortic Valve Closure (AVC) event on the basis of the M-shaped feature peak group;

determining an AVC feature point of the AVC event on the basis of the reference AVCT and the right shoulder second hemodynamic related information waveform;

performing second-order differential processing on the basis of the left shoulder second hemodynamic information waveform to generate a second-order differential graph; and setting the highest peak in one cardiac cycle of the second-order differential graph as an Aortic Valve Opening (AVO) feature point of the AVO event.

12. The cardiac physiological parameter measurement method of claim 11, wherein the processor executes the instructions to perform further steps comprising:

synchronizing the left shoulder second hemodynamic related information waveform and the right shoulder second hemodynamic related information waveform on the same time axis; and determining a Left Ventricular Ejection Time (LVET) on the basis of an Aortic Valve Opening Time (AVOT) of the AVO feature point and an AVCT of the AVC feature point in the same cardiac cycle.

13. The cardiac physiological parameter measurement method of claim 12, wherein the processor executes the instructions to perform a further step comprising:

outputting the LVET and/or the AVC feature point and/or the AVO feature point on a display connected with the processor.

* * * * *